United States Patent [19]

Spero et al.

[11] Patent Number: 6,043,376

[45] Date of Patent: Mar. 28, 2000

[54] SYNTHESIS OF ALPHA-METHYL, ALPHA-SUBSTITUTED AMINO ACIDS

[75] Inventors: Denice M. Spero, West Redding; Suresh Kapadia, Danbury, both of Conn.; Elio Napolitano, Pisa, Italy

[73] Assignee: Boehringer Ingelheim Pharmaceuticals, Inc., Ridgefield, Conn.

[21] Appl. No.: 09/342,662

[22] Filed: Jun. 29, 1999

Related U.S. Application Data

[60] Provisional application No. 60/095,507, Aug. 6, 1998.

[51] Int. Cl.$^7$ .................................................. C07D 363/08
[52] U.S. Cl. ............................................................ 548/228
[58] Field of Search ............................................. 548/228

[56] References Cited

U.S. PATENT DOCUMENTS 4,508,921   4/1985   Amato et al. .

FOREIGN PATENT DOCUMENTS

WO98/39303   9/1998   WIPO .

OTHER PUBLICATIONS

Seebach, Et Al; Self–generation of Stereocenters (SRS)–Applications, Limitations, and Abandonment of a Synthetic Principle; Angew–Chem. Int. Ed. Engl, 1996, vol. 35, p. 2708, Pub. Wiley–VCH Verlag GmbH; Germany.

Seebach, Et Al; N,O–Acetals from Pivalaldehyde and Amino Acids for the x–Alkylation with Self–Reproduction of the Center of Chiralty. Enolates of 3 Benzoyl–2–(tert–butyl)–1,3–oxazolidin–5–ones; Helvetica Chimica Acta, 1985; vol. 68, p. 1243; Pub. Verlag Helvetica Chimica Acta AG; Switzerland.

Karady, Et Al; Enantioretentive Alkylation of Acyclic Amino Acids; Tetrahedron Letters; 1984; vol. 25, No. 39, pp. 4337–4340; Pub. Elsevier Science Pub. Co., Inc., Great Britain.

Fadel, Et Al; a–Alkylation of Acyclic Amino Acids with Self–Reproduction of the Center of Chirality. A new route to (S)–(+)–a–Alkylated Aspartic Acids;Tetrahedron Letters; 1987; vol. 28, No. 20, pp. 2243–2246; Pub. Elsevier Science Pub. Co.; Great Britain.

Altmann, Et Al; Versatile Stereoselective Synthesis of Completely Protected Trifunctional x–Methylated x–Amino Acids Starting From Alanine; Helvetica Chimica Acta; 1991; vol. 74, p. 800; Pub.Verlag Helvetica Chimica Acta AG, Switzerland.

Lavergne, Et Al; Synthese enantioselective d'a–aryl amino acides: substitution nucleophile aromatique sur le fluorobenzene chrome tricarbonyle d'enolates chiraux; J. Organomet. Chem., 1991; vol. 401, p. C10; Pub.Elsevier Science Pub. Co., Inc.;USA.

Mutter, Et Al;Stereoselective Synthesis Of Isovaline (IVA) And IVA–Containing Dipeptides For Use In Peptide Synthesis; Tetrahedron Letters; 1988; vol. 44, p. 4793; Pub.Elsevier Science Pub. Co., Inc.; Great Britain.

Alonso, Et Al;Enantiospecific Conversion of (S)–Alanine to (R)–a–Methyl Phenylalanine; Tetrahedron Asymmetry; 1995; vol. 6, p. 353; Pub. Elsevier Science Ltd;Great Britain.

Neuenswchwander, Et Al; Chloracylierung und Bromacylierung von Carbonylverbindungen: Eine in Vergessenheit geratene Carbonylreaktion. I. Praeparative Anwendungsbreite; Helvetica Chimica Acta; 1978; vol. 61, p. 2047; Pub. Verlag Helvetica Chimica Acta AG; Switzerland.

*Primary Examiner*—Gary Geist
*Assistant Examiner*—Brian J. Davis
*Attorney, Agent, or Firm*—Robert P. Raymond; Alan Stempel; Mary-Ellen M. Devlin

[57] ABSTRACT

An improved process for making chiral, α-methylated, α-substituted amino acids of the formula I

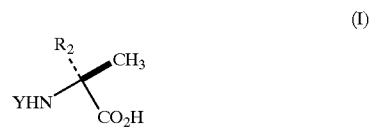

(I)

wherein Y is a hydrogen atom and $R_2$ is the residue of a natural or unnatural amino acid, in which process an oxazolidinone of the formula II

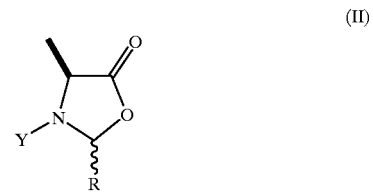

(II)

is formed by reacting a protected amino acid of the formula IA

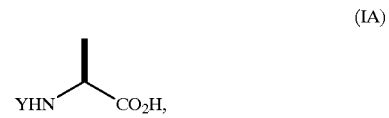

(IA)

wherein Y is a protecting group, with an aldehyde of the formula RCHO, or an equivalent thereof, in the presence of a chlorinating agent and a Lewis acid.

The group $R_2$ is introduced into the oxazolidinone intermediate of formula II in a conventional manner, and subsequent hydrolysis and deprotection, both carried out in a conventional manner, yield the chiral, α-methylated, α-substituted amino acid.

9 Claims, No Drawings

SYNTHESIS OF ALPHA-METHYL, ALPHA-SUBSTITUTED AMINO ACIDS

RELATED APPLICATIONS

Benefit of prior Provisional Application Ser. No. 60/095,507 filed Aug. 6, 1998 is hereby claimed.

FIELD OF THE INVENTION

The present invention relates to an improved method for making optically active α-methyl, α-substituted amino acids by enantioretentive substitution of optically active amino acids.

BACKGROUND OF THE INVENTION

Amino acids are carboxylic acids with an amino group at the α or C-2 position. They have the general formula $RCH(NH_2)CO_2H$. Except for glycine, wherein R is H, all have a center of asymmetry at the α position, and thus can exist in either of two enantiomeric forms (the D and the L configurations). The naturally occurring amino acids are in the L configuration. That is, they have the following projection formula.

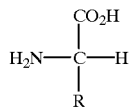

Optically active a-methylated amino acid analogs (compounds of the above formula wherein H is replaced by methyl and R is a residue corresponding to a natural or unnatural amino acid), particularly those having the L enantiomeric configuration corresponding to the naturally occurring amino acids, are known to be useful for a variety of purposes. Some α-methylated amino acids, such as for example methyldopa (L-α-methyl-3,4-dihydroxyphenylalanine), are useful as therapeutic agents. Others can be used as intermediates for the production of other useful substances. For example, as described in International Application No. PCT/US98/04254, α-methylated amino acid analogs can be used as intermediates to make certain hydantoins that are useful for treating or preventing inflammatory and immune cell-mediated diseases.

The prior art provides two general approaches for the synthesis of optically active α-methylated amino acids (and amino acid esters). The first general approach is to prepare a racemic product and then resolve the enantiomers. The second general approach, sometimes termed the enantioretentive approach, starts with an optically active α-amino acid and replaces the α-hydrogen while retaining, in the final product, the initial enantiomeric configuration.

A known method for the enantioretentive α-alkylation of amino acids takes advantage of a technique called the "self-regeneration of stereocenters", first introduced by Seebach et al. (*Angew. Chem. Int. Ed. Engl.* 1996, 35, 2708). This method is depicted in Scheme 1, below, for the amino acid alanine.

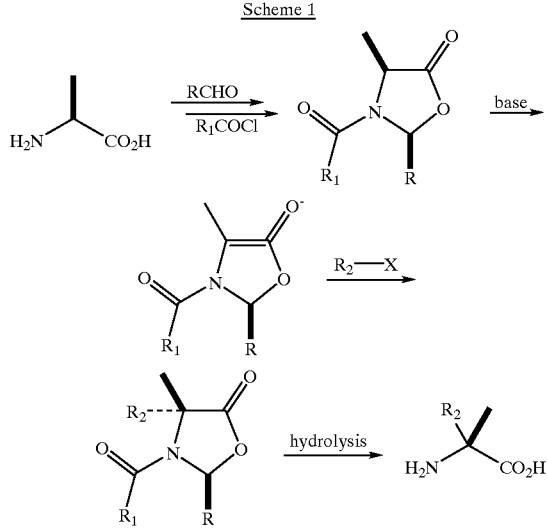

Scheme 1

In accordance with this technique, an optically pure amino acid containing one stereogenic center is reacted with an aldehyde (or aldehyde equivalent) to form an oxazolidinone having a second stereogenic center. Two isomers of the acetal are possible, but the formation of the cis isomer is usually preferred. (As the optical purity of the final product depends on the diastereomeric purity of the acetal, the unwanted trans isomer is usually removed, as by recrystallization or chromatography.) Reaction of the acetal with a base yields an enolate (such as, for example, the Li-enolate) in which the original stereogenic center has been destroyed (turned into a trigonal center), but in which chirality has been retained due to the second stereogenic center previously introduced. Reaction of the enolate with an electrophile results in the formation of an alkylated oxazolidinone. Alkylation, which takes place at the trigonal center, proceeds diastereoselectively, due to the influence of the second stereogenic center. Subsequent hydrolysis of the alkylated oxazolidinone yields an a-alkylated amino acid in which the absolute configuration of the original chiral center has been retained.

It will be noted that this synthetic technique essentially comprises three steps. The first step creates, as a key intermediate, an oxazolidinone template of the general formula

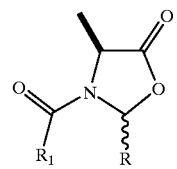

wherein R is part of an additional stereogenic center contributed by the aldehyde or aldehyde equivalent and $R_1CO$— is an appropriate protecting group. The second step involves alkylation of the oxazolidinone template with a base and an alkyl halide. The third step involves transformation of the N-protected and alkylated oxazolidinone into the desired α-methylated amino acid.

With respect to the first step, it should be noted that the literature provides two related approaches to the production of the oxazolidinone template. The two methods, depicted in Schemes 2 and 3, below, differ only in the order of introduction of the reagents.

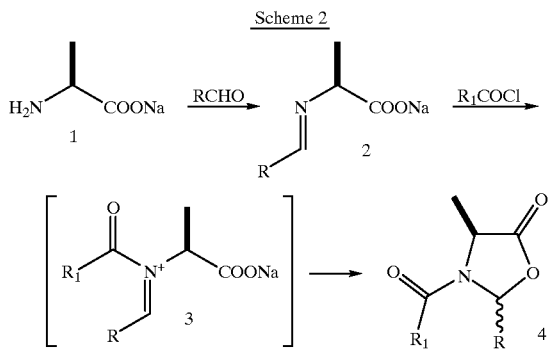

Scheme 2

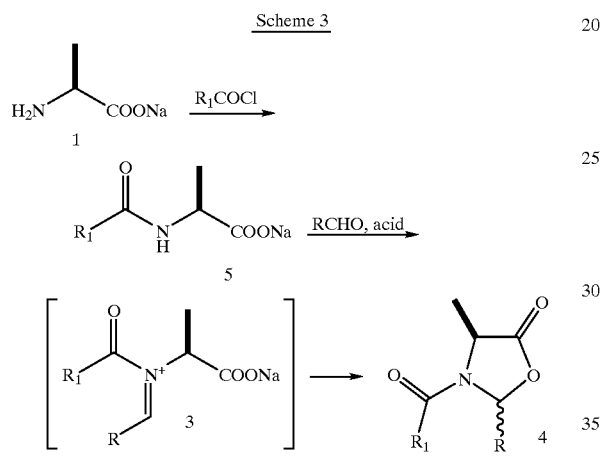

Scheme 3

In the first method (Scheme 2), originally described by Seebach (*Helv. Chim. Acta* 1985, 68,1243) the amino acid sodium salt 1 is treated first with an aldehyde to yield Schiff base 2. Acylation of this species presumably yields an intermediate acyliminium ion, 3, which then undergoes attack by the internal nucleophile, the carboxylate anion, thus forming the cyclic oxazolidinone template 4.

In the second method (Scheme 3), first described by Karady (Tetrahedron Lett. 1984, 25, 4337; U.S. Pat. No. 4,508,921), the same amino acid salt is first acylated, then activated by condensation with an aldehyde or equivalent, presumably to the same acyliminium ion 3, which then cyclizes as above.

As noted above, the utility of these procedures strongly depends on the ability to reproducibly and predictably generate a well-defined stereochemical relationship (cis or trans) between the α-methyl group and the new stereogenic center in 4. Both methods are unsatisfactory in this respect.

For example, by using the method of Scheme 2, Seebach et al. (*Helv. Chim. Acta* 1985, 68, 1243) reports a high yield of 4 (92%) but only a modest selectivity (2.5:1 to 5: 1) in favor of the cis isomer, depending for unclear reasons on the specific experimental protocol employed (R=tBu; $R^1$=Ph). By using the same method, Fadel et al. (*Tetrahedron Lett.* 1987, 28, 2243) also find variable ratios of cis/trans always favoring the cis isomer (from 3:1 to 7.5: 1) in high chemical yield (94%, R=$R^1$=Ph). On the other hand, Mutter et al. (*Helv. Chim. Acta* 1991, 74, 800) use this method to obtain a mixture of isomers favoring the trans isomer (2.5:1; R=Ph, $R^1$=PhCH$_2$O). Lavergne et al. (*J. Organomet. Chem.* 1991, 401, C10) obtain, by the same method, a good yield (81%) of a 3:1 cis:trans mixture. Mutter et al. (*Tetrahedron Lett.* 1988, 44, 4793) separately report on using the same method to obtain a low yield (50%) of the trans isomer exclusively (R=$R^1$=Ph). In direct contrast, Alonso et al. (*Tetrahedron Asymmetry* 1995, 6, 353) obtain only the cis isomer in good yield (92%), again using the same protocol (R=ferrocenyl, $R^1$=tBu). Accordingly, it is evident that Method A lacks in predictability and reproducibility, and can lead, under apparently similar conditions but slight structural changes in R and $R_1$, to cis/trans mixtures in any ratio ranging from only trans to only cis. The reasons for this inconsistent behavior have not been investigated.

Likewise, the method of Scheme 3, (*Tetrahedron Lett.* 1984, 25, 4337), employed less often, is also unsatisfactory because it proceeds in poor yield and gives a modest cis:trans ratio of 4:1 (R=2,4—Cl$_2$–C$_6$H$_3$; $R^1$=BnO).

SUMMARY OF THE INVENTION

The present invention provides an improved method for making optically active α-methylated, α-substituted amino acids by enantioretentive substitution of optically active amino acids. More specifically, the invention provides improvements upon the known method wherein there is first created an oxazolidinone template of the general formula

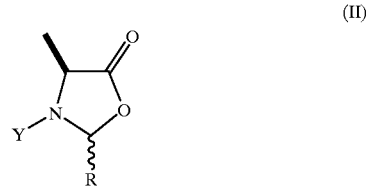

(II)

wherein R is part of an additional stereogenic center contributed by the aldehyde or aldehyde equivalent and Y is an appropriate protecting group; the oxazolidinone template is alkylated with a base and an alkyl halide; and, the N-protected and alkylated oxazolidinone is transformed into the desired α-methylated, α-substituted amino acid. In the improved process of the invention, an N-protected amino acid is condensed with an aldehyde or aldehyde equivalent in the presence of a chlorinating agent and a Lewis acid to form a cis oxazolidinone.

DETAILED DESCRIPTION OF THE INVENTION

The invention provides an improved process for making chiral, α-methylated, α-substituted amino acids of the formula I

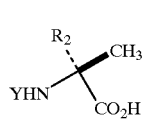

(I)

wherein Y is a hydrogen atom and $R_2$ is the residue of a natural or unnatural amino acid.

In accordance with the improved process of the invention, an oxazolidinone of the formula II

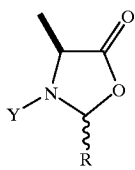

(II)

wherein R is part of a temporary, chiral or stereogenic center and Y is a typical amine protecting group, is formed by reacting a protected amino acid of the formula IA

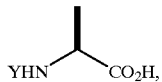

(IA)

wherein Y is the aforementioned protecting group, with an aldehyde of the formula RCHO, or an equivalent thereof, in the presence of a chlorinating agent and a Lewis acid. This is depicted below in Scheme 4.

Scheme 4

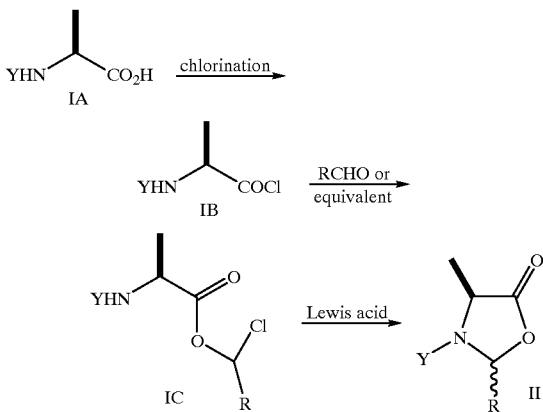

The method of the invention yields, reproducibly and in good yields, the cis form of the oxazolidinone of formula II, with high diastereoselectivity.

The method of the invention differs from the methods depicted in Schemes 2 and 3 in that the N-protected amino acid of formula IA is first chlorinated to yield an activated acid chloride derivative of formula IB, which is then condensed with an aldehyde or aldehyde equivalent.

The chlorination and the condensation steps can be performed in one pot (simultaneously) or sequentially. The protected amino acid can be reacted, in one pot, with the chlorinating agent, aldehyde and Lewis acid, or the amino acid can first be reacted with the chlorinating agent to yield the corresponding acid chloride, and the acid chloride can then be reacted with the aldehyde and Lewis acid to yield the oxazolidinone. That is to say, there are two variants of the process according to the invention. According to the first process variant, the protected amino acid of formula IA, the chlorinating agent, aldehyde or acetal, and Lewis acid are introduced essentially simultaneously to the reaction mixture. According to the second process variant, the protected amino acid of formula IA and the chlorinating agent are first reacted to form the acid chloride and the aldehyde or acetal is thereafter reacted with the acid chloride in the presence of the Lewis acid. It has been found that he sequential method leads to slightly higher yields, but is more laborious. The one-pot method is simpler to carry out. Both variations are considered to be merely alternative embodiments of the invention. The acid chloride of formula IB need not be isolated.

As acid chlorides are known to react with aldehydes to yield α-chloroesters (ref.

M. Neuenswchwander et al. Helv. Chim. Acta 1978, 61, 2047), it is very likely that a species of formula IC is formed as an intermediate. No attempt has been made to isolate this intermediate.

Cyclization, presumably of the species of formula IC, is brought about by the Lewis acid.

The reaction, whether conducted in one or two steps, is conveniently carried out in a non-protic solvent, such as, for example, THF, TBME, diethyl ether, dioxane, glyme, dichloromethane, chloroform, acetonitrile, or toluene, at a temperature between about $-25$ and $50°$ C. The use of THF at about $0°$ C. is preferred.

The protecting group Y may be any known per se amine protecting group, such as, for example, those which together with the protected amine group form an carbamate group, those which together with the nitrogen atom form an amide group, and those which together with the nitrogen atom form an sulfonamide group. Exemplary protecting groups are those selected from the class consisting of methyloxycarbonyl, ethyloxycarbonyl, n-propyloxycarbonyl, n-butyloxycarbonyl, t-butyloxycarbonyl, isopropyloxycarbonyl, isobutyloxycarbonyl, 9-fluorenylmethyloxycarbonyl, 2,2,2-trichloroethyloxyearbonyl, 2-trimethylsilylethyloxycarbonyl, allyloxycarbonyl, benzyloxycarbonyl, diphenylmethyloxycarbonyl, acetyl, benzoyl, trifluoroacetyl, phenylacetyl, trichloroacetyl, chloroacetyl, p-toluenesulfonyl, methanesulfonyl, and triflyl.

Suitable chlorinating agents for forming the acid chloride of formula IB are oxalyl chloride, thionyl chloride, phosphorus pentachloride and other agents routinely used for the conversion of carboxylic acids to acid chlorides.

The nature of the group R is not critical, as it merely serves as part of an additional, and temporary, chiral center. Likewise, the nature of the aldehyde or aldehyde equivalent is not critical, as it merely serves as a source of this additional and temporary chiral center.

The group R may suitably be, for example, $C_{1-10}$ alkyl, $C_{3-10}$ cycloalkyl, $C_{2-10}$ alkenyl or alkynyl, or an aryl group selected from the class consisting of phenyl, napththyl, phenanthryl, anthryl, pyrrolyl, thienyl, furyl, pyridyl, pyrimidyl, pyrazinyl, triazinyl, imidazolyl, thiazolyl, oxazolyl, isoxazolyl, indolyl, puryl, quinolyl, and isoquinolyl, wherein said aryl group is unsubstituted or mono-, di or tri-substituted with $C_{1-10}$ alkyl, $C_{3-10}$ cycloalkyl, $C_{2-10}$ alkenyl or alkynyl; trifluoromethyl, cyano, acetyl, trifluoroacetyl, carboxamido, methoxycarbonyl, ethoxycarbonyl, amino, methylamino, dimethylamino, acetamido, nitro, methoxy, ethoxy, phenoxy, acetyloxy, benzyloxy, fluoro, chloro, bromo, iodo, thiomethoxy, methylsulfinyl.

Suitable aldehydes are, for example, those of the formula RCHO wherein R is as defined above.

Suitable aldehyde equivalents are acetals of the formula $RCH(OR_2)$ wherein R is defined as above and $R_2$ is $C_{1-10}$ alkyl or phenyl (which is unsubstituted or mono-, di or tri-substituted with $C_{1-10}$ alkyl, $C_{3-10}$ cycloalkyl, $C_{2-10}$ alkenyl or alkynyl; trifluoromethyl, cyano, acetyl, trifluoroacetyl, carboxamido, methoxycarbonyl, ethoxycarbonyl, amino, methylamino, dimethylamino, acetamido, nitro, methoxy, ethoxy, phenoxy, acetyloxy, benzyloxy, fluoro, chloro, bromo, iodo, thiomethoxy, methylsulfinyl), and cyclic acetals of the formula

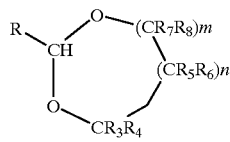

wherein R is as hereinbefore defined, $R_3$–$R_8$ are each, independently, hydrogen or methyl, and n—m=0, 1 or 2.

Exemplary aldehydes are benzaldehyde, p-phenyl benzaldehyde, pivalaldehyde, isobutyraldehyde, valeraldehyde, cinnamaldehyde, acrolein, anthranylaldehyde, 1- and 2-napththalenecarboxaldehyde, 2- and 3-thienyl, pyrryl or furyl carboxaldehyde, and 2-, 3- and 4-pyridyl carboxaldehyde. Exemplary aldehyde equivalents are the corresponding acetals from the lower alcohols methanol, ethanol, butanol and ethylene glycol.

Preferred aldehydes are benzaldehyde, p-phenyl benzaldehyde, pivalaldehyde and isobutyraldehyde.

Correspondingly, exemplars of R are phenyl, 4-phenylphenyl, t-butyl, isopropyl, butyl, 2-phenyl-1-ethenyl, ethenyl, 2-aminophenyl, 1- and 2-naphthyl, 2- and 3-thienyl, 2- and 3-pyrryl, 2- and 3-furyl, and 2,3 and 4-pyridyl.

It is correspondingly preferred that R be phenyl, 4-phenylphenyl, t-butyl or isopropyl.

Suitable Lewis acids are tin tetrachloride and tetrabromide, zinc chloride, bromide and iodide, boron trifluoride, trichloride and tribromide, aluminum trichloride and tribromide, titanium tetrachloride and tetrabromide. The preferred Lewis acid is $ZnCl_2$, which has been found to lead to a consistently high level of cis isomer. Cis:trans selectivities are typically of the order of 20:1 to 40:1, depending on the specific R and Y.

The oxazoliditone of formula II, which may optionally be purified by recrystallization or similar technique, can be reacted with a suitable alkyl halide, in a known per se manner, to yield an alkylated oxazolidinone of the formula III, below, wherein $R_2$ is the alkyl group so introduced.

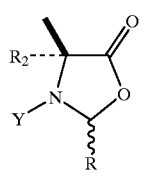

(III)

The identity of the alkyl halide used will be governed by the identity of $R_2$ in the desired α-methyl, α-substituted amino acid end product of formula I.

Hydrolysis of the intermediate of formula III is accomplished in a known per se manner, using acidic or basic conditions, to yield the final product of formula I. This may be accomplished using, for example, NaOH or HBr in AcOH. The protecting group Y may be removed from the product of formula I in a known per se manner.

The following examples will further illustrate the invention.

EXAMPLE 1

One-pot Method

Step 1

Preparation of cis-3-carbobenzyloxy-4-methyl-2-phenyloxazolidinone $SOCl_2$ (0.65 ml, 8.96 mmol) was added to a stirring solution of (S)-N-carbobenzyloxy alanine (2.0 g. 8.96 mmol) and benzaldehyde dimethyl acetal (1.34 ml, 8.96 mmol) in dry THF (15 ml) at 0° C. After stirring for 5 min, anhydrous $ZnCl_2$ (1.22 g, 8.96 mmol) was added and the reaction mixture was stirred at this temperature for 3 h. At this stage, 0.2 eq. each of $SOCl_2$ (0.13 ml) and anhydrous $ZnCl_2$ (0.25 g) were added and the reaction mixture was stirred for 1 h. The reaction was followed by silica gel TLC (20% ethyl acetate/hexane, $R_f$~0.5).

The reaction mixture was quenched by dropwise addition of water so that the reaction temperature did not exceed 10° C. It was extracted with ethyl acetate. The organic extract was washed with water until almost neutral, washed with sat. $NaHCO_3$ solution, water and finally dried over anhydrous $Na_2SO_4$. Evaporation of the solvent furnished a light yellow oil that solidified on stirring with 18 ml of hexane. The product was filtered and dried under reduced pressure (1.81 g, 65%, 29:1 cis/tans by NMR).

The product was purified by crystallization from ethanol/water to give colorless needles, mp 52° C.–53° C. (1.46 g, 52.3%>50:1 cis by NMR). An alternative workup is to dissolve the crude template in EtOH and then add to a mixture of $EtOH/H_2O$ at 0° C. The product precipitates out of solution in 48% yield with a high cis/trans ratio.

Step 2

Preparation of Cis-4-(4-bromobenzyl)-3-carbobenzyloxy-4-methyl-2phenyloxazolidinone A solution of cis-carbobenzyloxy-4-methyl-2-phenyloxazolidinone (51.62 g, 0.166 mol) and 4-bromobenzyl bromide (41.41 g, 0.166 mol) in dry THF (100 ml) was added to a stirring solution of KHMDS/Tol. (0.38 M, 0.174 mol, 457 ml, 1.05 eq.) in dry THF (400 ml) at −30° C. at such a rate that the internal temperature remained between −27.5° C. and −26.5° C. The addition was complete in 1.5 h. The reaction mixture was stirred at this temperature for 1 h followed by stirring at room temperature for 1 h. The progress of the reaction was followed by silica gel TLC with 10% ethyl acetate/hexane ($R_f$~0.4).

The reaction mixture was then poured into 1 L of ice cold saturated $NaHCO_3$ and extracted with 700 ml of ethyl acetate. The organic layer was separated, dried over anhydrous $Na_2SO_4$ and the solvent was evaporated to give a light yellow oil (85.0 g).

Step 3

Preparation of (R)-α(4-Bromobenzyl)-alanine hydrobromide

30% HBr/acetic acid (100 ml) was added over 0.33 h to a stirring solution of crude cis-4-(4-bromobenzyl)-3-carbobenzyloxy-4-methyl-2-phenyloxazolidinone (85.0 g) in glacial acetic acid (150 ml) at room temperature and the reaction mixture was stirred for 20 h.

Solvent was evaporated and the residue was dissolved in 600 ml of water. 100 ml of 2N HBr was also added. It was extracted with 600 ml of ethyl acetate which was discarded. The aqueous phase was evaporated to dryness to give an off-white solid (49.2 g).

Step 4

Preparation of (R)-α(4-Bromobenzyl)-alanine ethyl ester

HCl gas was bubbled through a solution of the crude (R)-α-(4-bromobenzyl)-alanine hydrobromide (949.2 g) in ethyl alcohol (200 proof) at room temperature for 0.75 h. During this time, the reaction temperature went up to 45° C. The reaction mixture was stirred at 70° C. (bath temp.) for 24 h. Since the reaction was incomplete, more HCl gas was bubbled (0.25 h) and the reaction mixture was stirred for an additional 10 h at 70° C.

After evaporation of the alcohol, the residue was dissolved in 250 ml of water and extracted with 300 ml of ethyl acetate. The organic extract was discarded. The aqueous phase was basified with solid $NaHCO_3$ and the product was extracted with $CH_2Cl_2$. The organic phase was dried over anhydrous $Na_2SO_4$ and concentrated to a light brown oil which solidified on standing. The product was purified by crystallization from light pet. ether, mp 42° C.–43° C. (31.5 g, 66% over three steps, chemical purity 95%, ee>99%).

EXAMPLE 2

Two-pot method

Step 1

Preparation of 3-Isobutoxycarbonyl-2-(4-phenyl-4methyl)-5-oxazolidinone.

N-Isobutoxycarbonyl alanine (53 g, 0.3 mol), dimethylformamide (2 mL) were dissolved in methylene chloride (300 mL) under magnetic stirring and the solution cooled at about 10° C. Oxalyl chloride (30 mL, 0.33 mol) was added over 15 min (gas evolution); the mixture was then allowed to equilibrate with room temperature. After 1 h, 4-biphenylcarbaldehyde (54 g, 0.3 mol) was added (slight endothermic reaction); when dissolution was complete, the reaction mixture was cooled by means of a ice-water bath; when the internal temperature was at about 15° C., $ZnCl_2$ (beads from Aldrich, 1 g) was added. The ice bath was then removed and the solution stirred at the room temperature for 3 h. A slow stream of nitrogen was passed to remove HCl formed in the reaction, which caused some concentration of the mixture and precipitation of 3 as a creamy solid from the reddish solution. Hexane (200 mL) was added and mixture cooled again to complete the formation of the precipitate that was red in color. The precipitate was collected on a buchner, covered with tert-butyl methyl ether and triturated until the red color was discharged and precipitate turned off-white. Suction of the solvent left 81 g, (75%) of isomerically pure product.

Step 2

Preparation of 3-Isobutoxycarbonyl-2-biphenyl-4-methyl-4-p-bromobenzyl-5-oxazolidinone (10 g, 28.3 mmol), p-bromobenzylbromide (8.1 g, 32.5 mmol) was suspended in 50 mL of THF and after 15 min stirring under nitrogen, the mixture was cooled to keep the internal temperature between −25 and −30° C. Lithium bistrimethylsiylamide (32 mL of a 1 M solution in hexane) was added dropwise over 30 min; the mixture stirred for 30 min at −25° C., then allowed to equilibrate to room temperature over 30 min. The mixture became homogeneous and then turbid. The mixture was diluted with hexane (100 mL) containing some t-butyl methyl ether to help solubilization, and extracted with 100 mL of water containing 4 mL of concentrated HCl. The organic phase was washed with brine, dried and evaporated to give a residue (16 g, >100% yield) of product.

What is claimed is:

1. A process for producing an oxazolidinone of the formula II

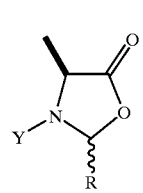

(II)

wherein

R is $C_{1-0}$ alkyl, $C_{3-10}$ cycloalkyl, $C_{2-10}$ alkenyl or alkynyl, or an aryl group selected from the class consisting of phenyl, napthyl, phenanthryl, anthryl, pyrrolyl, thienyl, furyl, pyridyl, pyrimidyl, pyrazinyl, triazinyl, imidazolyl, thiazolyl, oxazolyl, isoxazolyl, indolyl, puryl, quinolyl, and isoquinolyl, wherein said aryl group is unsubstituted or mono-, di or tri-substituted with $C_{1-10}$ alkyl, $C_{3-10}$ cycloalkyl, $C_{2-10}$ alkenyl or alkynyl; trifluoromethyl, cyano, acetyl, trifluoroacetyl, carboxamido, methoxycarbonyl, ethoxycarbonyl, amino, methylamino, dimethylamine, acetamido, nitro, methoxy, ethoxy, phenoxy, acetyloxy, benzyloxy, fluoro, chloro, bromo, iodo, thiomethoxy or methylsulfinyl, and Y is an amine protecting group, which process comprises:

reacting a protected amino acid of the formula IA

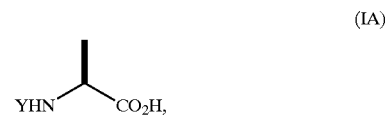

(IA)

wherein Y is as hereinbefore defined, with a chlorinating agent, to form the corresponding acid chloride, and reacting the acid chloride with an aldehyde of the formula RCHO, wherein R is as hereinbefore defined, or with an acetal of the formula $RCH(OR_2)$ wherein R is defined as above and $R_2$ is $C_{1-10}$ alkyl or phenyl (which is unsubstituted or mono-, di or tri-substituted with $Cl_{1-10}$ alkyl, $C_{3-10}$) cycloalkyl, $C_{2-10}$ alkenyl or alkynyl; trifluoromethyl, cyano, acetyl, trifluoroacetyl, carboxamido, methoxycarbonyl, ethoxycarbonyl, amino, methylamino, dimethylamino, acetamido, nitro, methoxy, ethoxy, phenoxy, acetyloxy, benzyloxy, fluoro, chloro, bromo, iodo, thiomethoxy, methylsulfinyl, or with a cyclic acetal of the formula

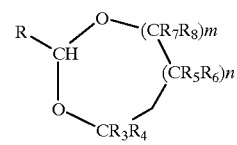

wherein R is as hereinbefore defined, $R_3$–$R_8$ are each, independently, hydrogen or methyl, and n+m=0, 1 or 2, in the presence of a Lewis acid.

2. The process of claim 1 wherein the protected amino acid of formula IA, the chlorinating agent, aldehyde or acetal, and Lewis acid are introduced essentially simultaneously to the reaction mixture.

3. The process of claim 1 wherein the protected amino acid of formula IA and the chlorinating agent are first reacted to form the acid chloride and the aldehyde or acetal is thereafter reacted with the acid chloride in the presence of the Lewis acid.

4. The process of claim 1, 2 or 3 wherein Y is a protecting group selected from the class consisting of methyloxycarbonyl, ethyloxycarbonyl, n-propyloxycarbonyl, n-butyloxycarbonyl, t-butyloxycarbonyl, isopropyloxycarbonyl, isobutyloxycarbonyl, 9-fluorenylmethyloxycarbonyl, 2,2,2-trichloroethyloxycarbonyl, 2-trimethylsilylethyloxycarbonyl, allyloxycarbonyl, benzyloxycarbonyl, diphenylmethyloxycarbonyl, acetyl, benzoyl, trifluoroacetyl, phenylacetyl, trichloroacetyl, chloroacetyl, p-toluenesulfonyl, methanesulfonyl, and triflyl.

5. The process of claim 1, 2 or 3 wherein the chlorinating agent is selected from the class consisting of oxalyl chloride, thionyl chloride and phosphorus pentachloride.

6. The process of claim 1, 2 or 3, wherein:

the aldehyde or acetal is selected from the class consisting of benzaldehyde, p-phenyl benzaldehyde, pivalaldehyde, isobutyraldehyde, valeraldehyde, cinnamaldehyde, acrolein, anthranylaldehyde, 1- and 2-napththalenecarboxaldehyde, 2- and 3-thienyl, pyrryl or furyl carboxaldehyde, and 2-, 3- and 4-pyridyl carboxaldehyde, and the corresponding acetals formed from methanol, ethanol, butanol or ethylene glycol; and, R is, correspondingly, selected from the class consisting of phenyl, 4-phenylphenyl, t-butyl, isopropyl, butyl, 2-phenyl-1-ethenyl, ethenyl, 2aminophenyl, 1- and 2-naphthyl, 2- and 3-thienyl, 2- and 3-pyrryl, 2- and 3-furyl, and 2,3 and 4-pyridyl.

7. The process of claim 1, 2 or 3 wherein the aldehyde is selected from the class consisting of benzaldehyde, p-phenyl benzaldehyde, pivalaldehyde and isobutyraldehyde and R is, correspondingly, selected from the class consisting of phenyl, 4-phenylphenyl, t-butyl and isopropyl.

8. The process of claim 1, 2 or 3 wherein the Lewis acid is selected from the class consisting of tin tetrachloride and tetrabromide, zinc chloride, bromide and iodide, boron trifluoride, trichloride and tribromide, aluminum trichloride and tribromide, and titanium tetrachloride and tetrabromide.

9. The process of claim 1, 2 or 3 wherein the Lewis acid is $ZnCl_2$.

* * * * *